United States Patent [19]

Reid et al.

[11] 4,109,642
[45] Aug. 29, 1978

[54] APPARATUS FOR ULTRASONIC ARTERIOGRAPHY

[75] Inventors: John M. Reid; Merrill P. Spencer, both of Seattle, Wash.

[73] Assignee: Institute of Applied Physiology & Medicine, Seattle, Wash.

[21] Appl. No.: 454,423

[22] Filed: Mar. 25, 1974

Related U.S. Application Data

[63] Continuation-in-part of Ser. No. 240,349, Apr. 3, 1972, abandoned.

[51] Int. Cl.² .............................................. A61B 10/00
[52] U.S. Cl. ..................................... 128/2 V; 73/622; 128/2.05 Z
[58] Field of Search ............. 128/2 V, 2.05 Z, 2.05 F, 128/24 A; 73/67.6–67.8, 622

[56] References Cited

U.S. PATENT DOCUMENTS

| 3,023,611 | 3/1962 | Howry | 128/2 V X |
| 3,086,390 | 4/1963 | Brown | 128/2 V X |
| 3,090,030 | 5/1963 | Schuck | 340/16 R |
| 3,480,002 | 11/1969 | Flaherty et al. | 128/2 V |
| 3,577,772 | 5/1971 | Perilhou | 128/2 V |
| 3,690,311 | 9/1972 | Schorum et al. | 128/2 V |
| 3,777,740 | 12/1973 | Hokanson | 128/2 V |
| 3,778,756 | 12/1973 | Houston et al. | 128/2 V UX |
| 3,805,596 | 4/1974 | Klahr | 128/2 V UX |
| 3,827,115 | 8/1974 | Bom | 128/2 V X |

Primary Examiner—Kyle L. Howell
Attorney, Agent, or Firm—Seed, Berry, Vernon & Baynham

[57] ABSTRACT

Continuous wave ultrasonic sound waves from a transmitter and receiver are highly focused to a width of approximately 1 millimeter or less and are transmitted and received through intersecting paths within the tissue of a patient. A doppler flow detector produces an image of the moving blood within the vessel. The transmitter and receiver are systematically scanned over the subject and the detected images are converted into visually intelligible pictures.

An improved circuit for more clearly defining the flow picture of the moving blood particles utilizes a conventional directional doppler circuit plus a multiplier-differentiator-low pass filter circuit to automatically eliminate venous flow signals. A grey scale oscilloscope provides brightness intensity on the visual picture proportional to the velocity and direction of the blood flow for detecting stenosis in the vessel.

A recording technique is disclosed for detecting atherosclerotic thickening of the artery wall.

A multiple beam scanner is disclosed which requires movement only in the longitudinal direction of the vessel.

24 Claims, 16 Drawing Figures

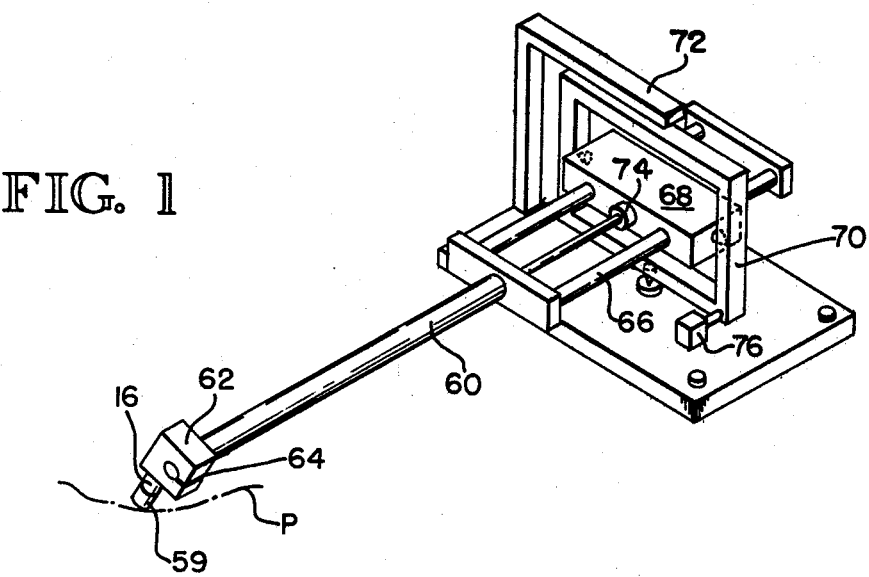
FIG. 1
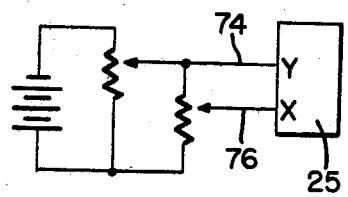
FIG. 2
FIG. 4
FIG. 3
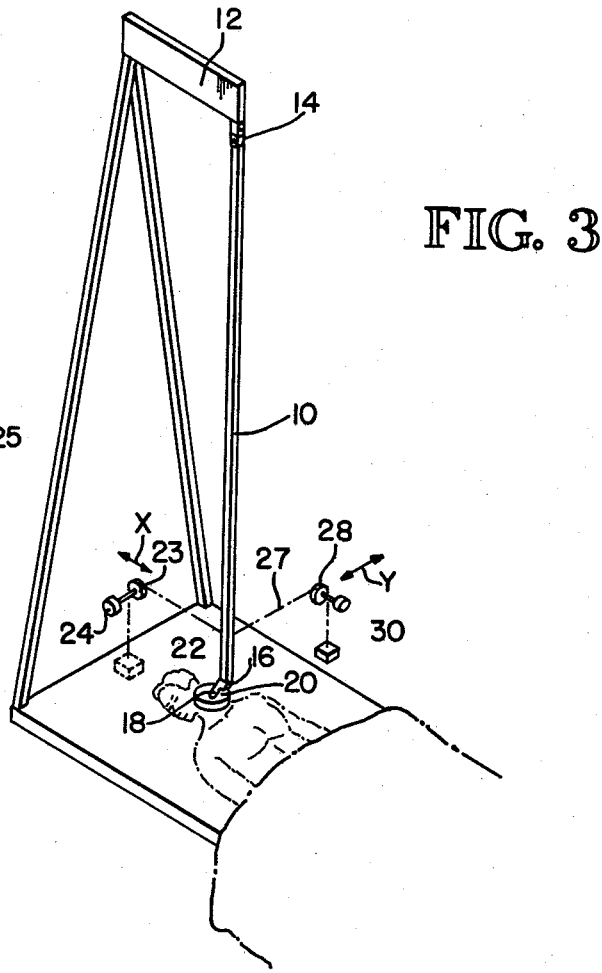

FLOW MAP

ARTERY
SCAN DIRECTION

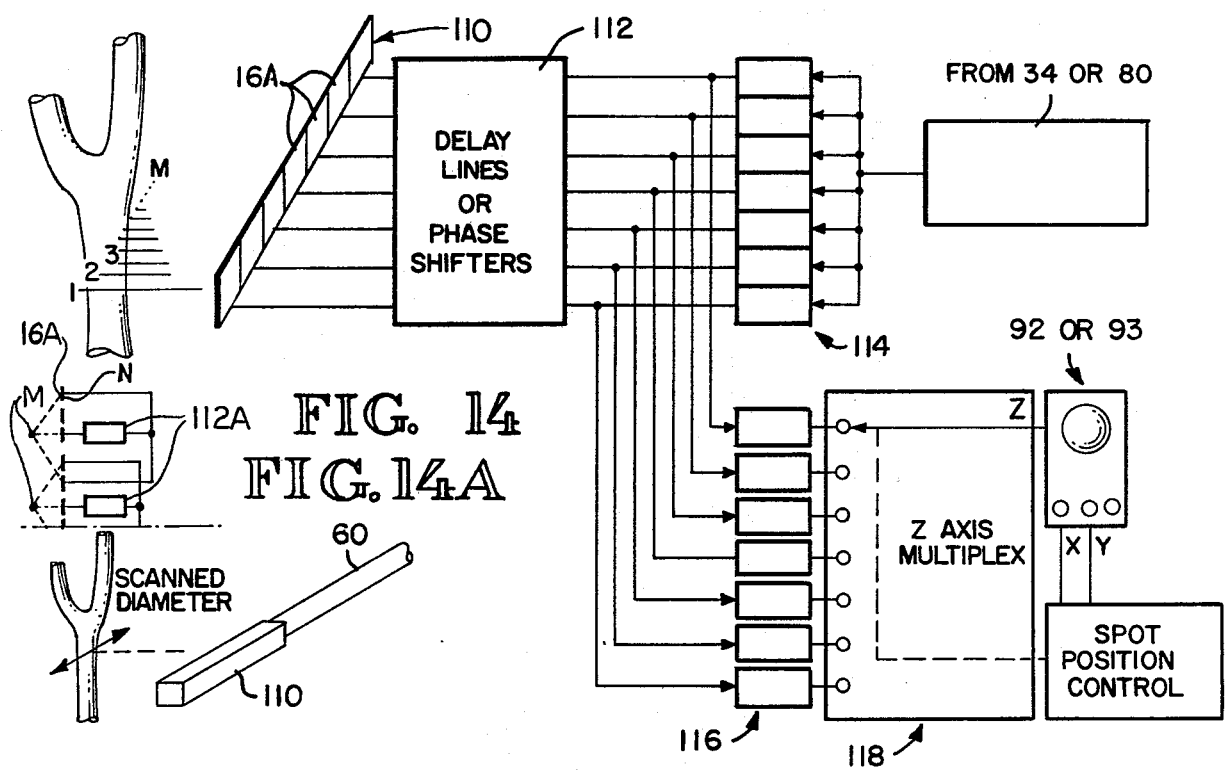
FIG. 14
FIG. 14A
FIG. 10
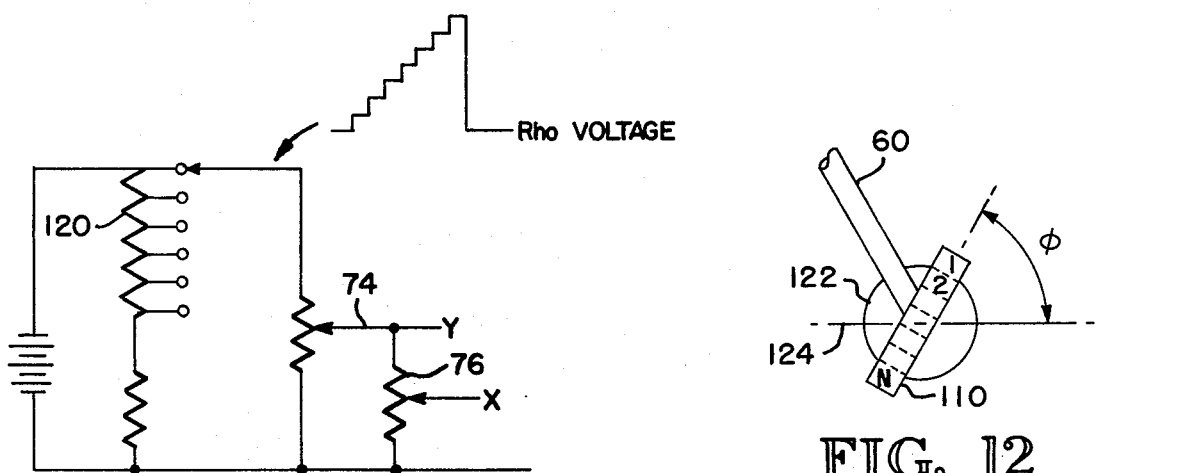
FIG. 11
FIG. 12
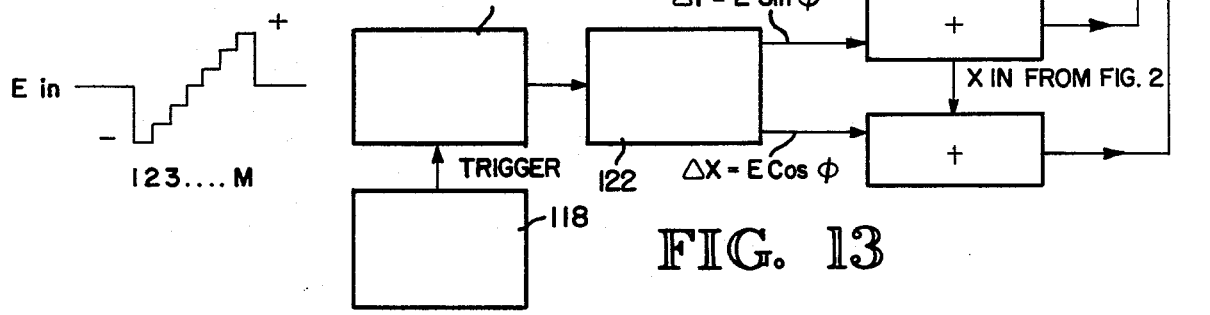
FIG. 13

APPARATUS FOR ULTRASONIC ARTERIOGRAPHY

CROSS-REFERENCE TO RELATED APPLICATION

This application is a continuation-in-part of our earlier application Ser. No. 240,349, filed Apr. 3, 1972, now abandoned.

BACKGROUND OF THE INVENTION

1. Field of the Invention

This invention pertains to techniques for defining the shape, condition and function of blood vessels imbedded in human tissue.

2. Description of the Prior Art

Present commercial techniques utilize dye contrast radiography to produce arteriograms or venograms. Dye-contrast radiography requires that a radioopaque fluid be admitted into the bloodstream through the sidewall of the vessel, creating hazards to the health of the patient.

Continuous wave ultrasonic flow detectors using doppler techniques to detect the sound waves scattered from moving blood have been developed which avoid the necessity of introducing a fluid into the vessel and have given useful information when directed by hand and used to trace the circulation of animals and man. Continuous wave ultrasonic flow detectors in present use are generally limited to locating the blood vessels and determining the existence or non-existence of blood flow at various locations along the vessel. In part their use has been limited because it is generally believed that they encompass too great a region of tissue, i.e. lack adequate resolution, and are too difficult to direct for producing a picture equal in definition to that of dye-contrast radiographic arteriograms or venograms.

Pulsed ultrasonic doppler blood flow sensing is known. Known systems of this type, however, require extremely costly and sophisticated equipment and are very susceptible to signal noise when used to detect vessels deeply embedded in human tissue. Furthermore, the image produced shows the vessel along a plane perpendicular to the plane of the skin. This presents an immediate probelm of interpretation, since diagnosticians are more familiar with images parallel to the skin surface such as obtained from present state-of-the-art radiography.

SUMMARY OF THE INVENTION

It is an object of this invention to provide a method and apparatus for producing useful pictures of blood vessels in human tissue.

It is another object of this invention to provide an inexpensive apparatus for illustrating the image of a blood vessel in human tissue.

It is another object of this invention to provide a picture of a blood vessel in human tissue which is similar in appearance to conventional arteriograms.

Basically the invention comprises transmitting and receiving highly focused ultrasonic continuous sound waves into the tissue in which the vessel is located to a localized region at a particular depth to maximize their sensitivity to the exclusion of the surrounding regions, using a doppler detector to produce an output signal representative of the sound wave reflected only from the moving sound scatterers in the vessel, systematically scanning the transmitting and receiving means (manually or automatic electronic or mechanically) over the tissue to delineate a pattern of visual signals representative of the interior of the blood vessel, and converting the output signal to a visual form. The image is then preferably converted to a permanent record, such as by photographing the visual output as displayed on an oscilloscope.

The sound scatterers in the vessel are blood cells; however, other forms of scatterers, such as bubbles, particles, etc. can be employed.

Various techniques for maximizing the sensitivity of the sound waves at particular depths may be used, such as a plurality of transmitting and receiving transducers, phased array techniques including transmitting and receiving along coincident paths. In one embodiment illustrated a single transducer having highly focused, separated receiving and transmitting elements is employed. In another embodiment a plurality of closely spaced focused transducers or closely spaced transducers with delay lines or phase shifters are used to automatically produce a full diameter flow picture without moving the transducer transversely across the vessel.

The output signals received from the doppler flow detector can be shown visually immediately; the signal can be stored by computer, charge storage, thermal storage techniques, etc., and later reproduced visually; or both immediate and delayed visual images can be utilized.

Systematic scanning is obtained by manual-mechanical apparatus in the one illustrated embodiment but electronic or automatic mechanical scanning may also be employed.

Another object of the invention is to provide a clearer arterial flow picture by eliminating venous flow and intensifying the picture proportional to velocity of the blood for detecting stenosis.

This object is accomplished through the combination of a directional doppler system coupled with a grey scale, color scale or equivalent oscilloscope the intensity or color of which is determined by the velocity of the blood.

Another object of the invention is to detect atherosclerotic conditions of artery walls.

Another object is to detect atherosclerotic plaque, calcification and ulcerative conditions in the artery walls. This object is accomplished by detecting and separately recording low frequency-high amplitude sidewall vibration signals.

Another object is to identify the locus of turbulent flow and conditions for murmur formation.

BRIEF DESCRIPTION OF THE FIGURES OF THE DRAWING

FIG. 1 is one embodiment of an apparatus embodying the invention and useful for carrying out the method of this invention.

FIG. 2 is a portion of a circuit used with the apparatus of FIG. 1.

FIG. 3 is a more basic embodiment of apparatus and also suitable for carrying out the method of this invention.

FIG. 4 is a partial circuit for use with the apparatus of FIG. 3.

FIGS. 10-14A are diagrams illustrating a full diameter flow picture taking device.

DETAILED DESCRIPTION OF THE FIGURES OF THE DRAWINGS

A basic explanation of ultrasonic doppler blood flow sensing can be found in IEEE Transactions on Sonics and Ultrasonics, Vol. SU-17, No. 3, July 1970, pp 170-185. Details of the doppler flow detection are thus well known and will not be described in detail.

Figure 7A:
FIG. 7A is a typical idealized flow picture obtained by apparatus and circuits of FIGS. 1-6, it being understood that the dark lines actually appear as bright irregular lines on the oscilloscope and photograph of the oscilloscope picture.

FIG. 7A illustrates the picture obtained by an operator moving the transducer back and forth or by automatic scanning across the vessel while advancing along the vessel. The vessel thus is defined by a series of short bright scan lines of a length defined by the cross-section of the blood stream within the vessel. This provides a sharp outline of the bloodstream of high resolution in a plane readily understood by personnel familiar with arteriography. Stenosis in the plane of the scan is visualized by a shortening of the length of the scan lines. Heavy plaque buildup in the vessel walls will absorb much of the sound and appear in the picture as a void. Similarly, fully blocked vessels will also appear as a void and blood flow downstream of the blockage cannot be detected. Also, partly blocked vesels (stenosis) will produce turbulence downstream which produces a characteristic random doppler signal.

In FIG. 3 a basic apparatus for performing the invention is illustrated. A scanning bar 10 is suspended from a fixed mount 12 by a universal coupling 14. A conventional doppler blood flow detecting transducer 16 is secured to the free end of the bar. The particular transducer preferred is of the type illustrated in said IEEE publication at page 176 and utilizes a ⅜ inch diameter lead-zirconate-titanate element with the elements divided and at an angle to one another to provide separate sending and receiving areas. A spherical concave lens focuses the sound at a nominal three centimeters from the transducer and provides a 1-millimeter-wide field at the intersection of the receiving and transmitting focal points extending from about 2 to 4 centimeters in depth range. The transducer is then swung systematically across the vessels of interest while suspended at the end of the arm. In the form of FIG. 3 the transducer is submerged in a dish 18 containing a liquid which carries the sound waves directly to the skin of the patient. The dish is provided with a rubber bottom 20 to closely conform to the shape of the patient's skin. In this basic embodiment the transducer can thus be swung along the X and Y axes while maintaining sound transmitting contact with the patient's skin.

Also attached to the end of the arm is a wire 22 entrained about a pulley 23 which is connected to a conventional potentiometer 24. The free end of the wire is secured to a weight to keep a constant bias on the end of the wire. The potentiometer 24 is electrically connected to the X coordinate of an osciiloscope 25. A second wire 27 is also connected to the free end of the arm. The wire 27 is entrained about a pulley 28 which is connected to a potentiometer 30. A weight maintains a constant bias on the wire 27. The potentiometer 30 is electrically coupled to the Y coordinate of the oscilloscope 25. As is readily apparent, movement of the transducer back and forth to scan over the vessel being investigated directly deflects the spot on the cathode ray tube of the oscilloscope. The Z coordinate of the oscilloscope is provided by intensity modulation using the amplitude of the doppler shift frequency. In this manner a scanning pattern determined manually by an operator is followed to completely cover the area of the vessel being investigated. Since the operator can see the image being formed, he is able to shorten the scanning time somewhat by confining the scan to the immediate area of the vessel. A second memory oscilloscope is helpful for use by the operator during scanning. A 5 MHz carrier frequency for the doppler detector has been found best to record flow from vessels located behind several centimeters of muscle.

Figure 5:
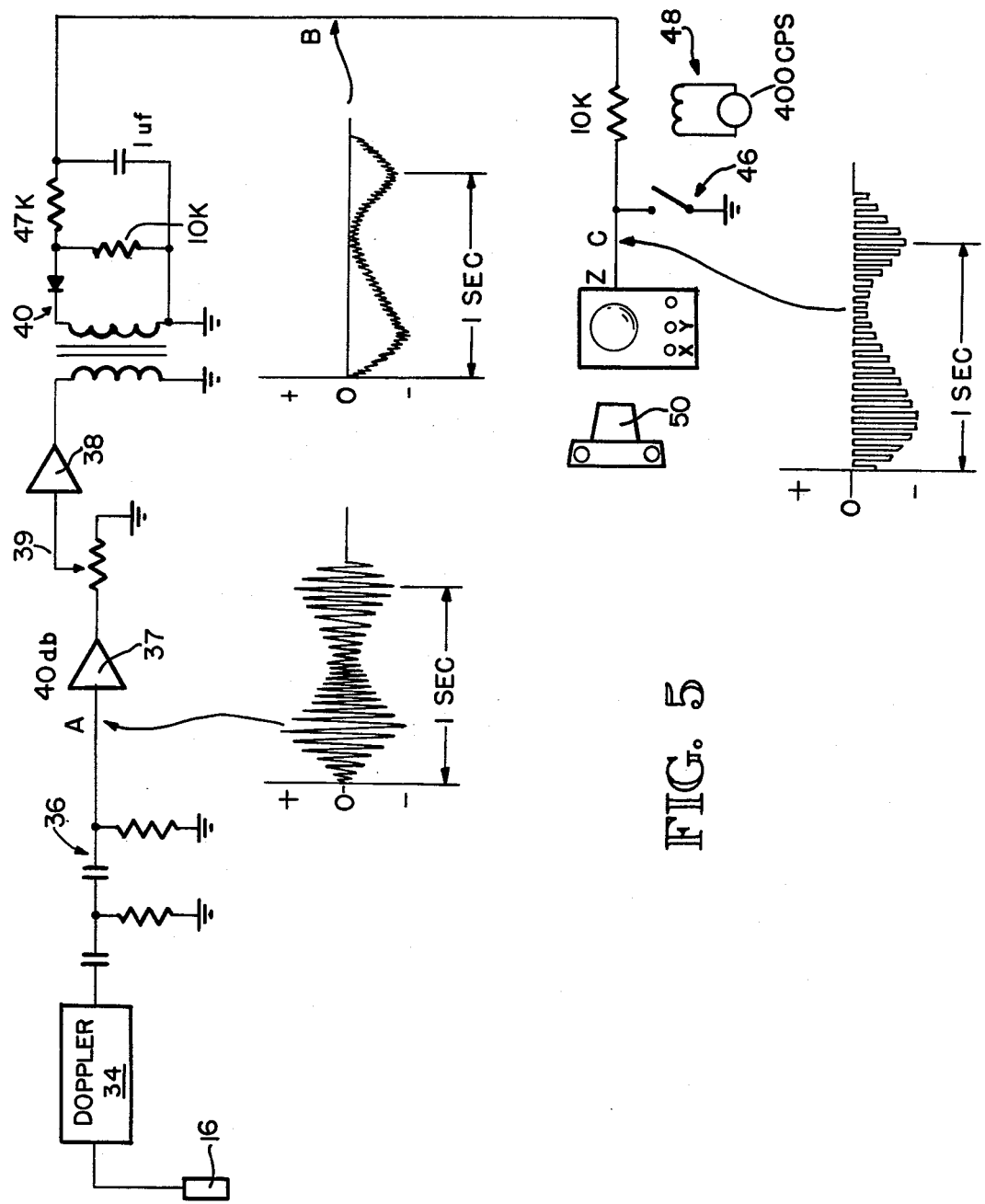
FIG. 5 is a block diagram of the electronic circuit used with the apparatus of FIG. 3 and with the apparatus of FIG. 1 with only slight alteration.

FIG. 5 illustrates a preferred electronic circuit for providing a visual output of the signals being detected in an arterial investigation. The transducer 16 is coupled to an ultrasonic doppler flow detector 34. Preferably the doppler unit is modified to employ a five megahertz carrier frequency to better enable it to penetrate muscle tissue than commercial units which operate at a higher frequency. The doppler sends the ultrasonic wave into the tissue through the transducer 16. Output signals from the doppler unit 34 represent reflections from the moving blood cells within the vessel or vessels within the depth range of the transducer.

It is necessary to separate arterial flow and venous flow, which could produce flow signals as well, such as occurs by the close proximity of the jugular vein and the carotid artery, for example. One solution is to use conventional directional doppler circuitry to construct a suitable flow-separating network. In such conventional circuitry the output of the two demodulators used for flow sensing is a pair of signals differing 90° in phase. The direction of flow is indicated by which channel leads the other. Rather than convert the doppler frequency into a voltage as commercial instruments do, this procedure obtains two separate outputs for flow toward and flow away from the transducer. This electrical problem is identical to the problem of separating the sidebands in a single sideband communication system and components can be used according to one of the methods found successful there, such as the use of a wideband audio phase-shift network to further rotate the phase. By this means a desired sideband, corresponding to flow in the desired direction, can be rotated to be in phase with a similar signal in the other channel and hence to add to it. The undesired sideband signal will be rotated to be out of phase with its twin in the other channel and hence will not appear in the output.

Interfering signals are also caused by motion of structures other than red blood cells. Two principal sources are the pulsatile motion of artery walls and structures near them and the relative movement between all body structures and the transducer caused by scanning. Control of the level of these signals is desirable, but recording of "stationary" structures probably will be desirable to establish anatomical landmarks in the picture. Both types of interference are controlled by the same means in present dopplers—filtering of the low frequency signals. Scanning motion interference can be reduced further by keeping the scanning speed low. This system will be free of the interference caused by bone shadows in conventional X-ray pictures, and thus allow scan planes to be chosen which result in the best flow visualization.

Within the doppler unit 34 of the preferred embodiment the received energy is rectified. The output of the rectifier is amplified by an audio frequency amplifier within the doppler unit. The response of this unit does not extend to low frequencies, thus in the preferred embodiment the only components which appear in the output of the doppler unit are those due to doppler frequency shift on the scattered energy caused by the motion of reflecting blood cells. All stationary structures return a wave at the same frequency that was transmitted and no audio frequency output results.

The output of the doppler unit 34 is fed through a two-section RC filter 36 to remove frequencies below 300 Hertz. This is done to remove flow signals from flow in the veins so that only arterial signals are recorded. As mentioned above, this is not an essential operation if a flow-direction sensing doppler unit is used. Thus, the filter is used mainly for convenience when not using a direction sensitive system. A typical wave form of a doppler signal is shown at A. It is a randomly varying audio frequency burst which looks like noise. It consists of frequencies above the cutoff frequency of the filter and less than the maximum doppler shift which could be caused by the moving blood. It appears in bursts because the heart is beating approximately once per second and the blood is moving only during a part of this time. The signal is passed to amplifier 37 and power amplifier 38 with the amplified signal controlled through a volume control 39 until it is of sufficient strength to be rectified in a rectifier circuit 40.

The function of the rectifier 40 is to produce a one-polarity signal for intensity modulating the cathode ray tube of the oscilloscope 25. The general appearance of the voltage after rectification is shown at B. The amount of random noise on the rectified wave form depends upon the amount of filtering performed following the rectifier. An R-C filter consisting of a 47,000 ohm resistor and a 1.0 microfarad capacitor is used. This combination smooths the wave form at the rectification and removes most of the pulses caused by noise from the building system and incidental motions of the patient or operator of the scanning system.

The signal at B cannot be applied directly to the cathode ray oscilloscope because of its extremely low frequency. Commercial oscilloscopes have an AC coupled Z-input circuitry which requires that the frequency be above a few hundred cycles per second. The signal is translated into this range by a synchronous switch 46, which is operated at a suitable rate by an audio generator 48. When the switch is closed, it shorts the voltage at the Z axis input terminal of the oscilloscope 25 to ground and when the switch is open, it allows the originally applied wave form as shown at B to be applied to the cathode ray tube. The result is the wave indicated generally at C. It consists of a series of rectangular bars whose tops generally follow the wave form shown at B and whose bottoms are the axis. Each of these negative joined bars acts as a pulse to turn on the cathode ray tube. Since the transducer probe is moved only very little between the individual bars, the different spots on the cathode ray tube overlap each other and the eye cannot detect that the chopping operation of the synchronous switch has been occurring.

The actual values of the filter and rectifier elements have been found through experimentation, although the best presently available may be improved upon.

A conventional memory oscilloscope is convenient to use. A permanent record can be obtained by a time exposure using a conventional camera 50 attached to a second oscilloscope also receiving the X, Y and Z inputs.

A more sophisticated preferred apparatus is illustrated in FIGS. 1 and 2. The basic apparatus is similar to that used for computerized mapping known as a "Rho-theta arm." Basically it includes an arm 60 to be mounted beside the patient P so that it will not restrict his motions and will allow the transducer to be swept by hand over the area of the skin on which the arteriogram is to be recorded. The arm will follow up and down contours without losing contact with the patient. A conventional solid coupling rod 59 or a conventional lens and jelly is used between the transducer and the patient to conduct the sound into and out of the patient. The scanning will thus be done without water and it is more convenient, faster and free of interfering signals than the apparatus shown in FIG. 3.

The scanning arm 60 is elongated, approximately 16 inches, to allow the trigonometric approximation that the sine of the angle theta, i.e. angular displacement in the horizontal plane, be approximately equal to theta and the cosine of the angle theta be approximately equal to 1. The arm 60 carries on its outer end a block 62 which supports the transducer 16. The block is slotted as at 64 to allow positioning of the block on the arm 60 to allow adjustment of the transducer angle with respect to the patient. The arm is connected by a pair of blocks to a second set of rods 66. The rods 66 have a sliding fit in a platform 68 which tilts about a horizontal axis. The sliding fit allows the arm to be slid in and out. The tilting platform 68 is mounted in a pivotal platform 70 which is pivotally mounted to a base 72. The base is attached to a table beside the patient and serves as a reference point for measuring the displacements of the transducer. Changes in length of the arm, that is, the Rho coordinate, are sensed by a conventional linear potentiometer 74 which is shown with its actuating rod connected to the arm 60. Motion of the transducer in the up and down direction is necessary to allow the transducer to ride over the various contours of the patient and is not transduced into the display of the cathode ray oscilloscope. The frame 70 carries the entire arm and is itself pivoted to the base. Angular motions of the entire scanning arm are detected by a Theta potentiometer 76 which is mounted on the base with its actuating arm connected to the rotatable frame 70. The Rho potentiometer is connected to the Y axis of the oscilloscope and the Theta potentiometer connected to the X axis of the oscilloscope. The Z coordinate is provided by intensity modulation using the doppler shift frequency as in the apparatus of FIG. 1.

In summary, it can be appreciated that the systematic scanning technique using highly focused intersecting receiving and transmitting paths allows one to make a positive identification of vessels from which flow recordings of velocity can be made of conventional constant wave doppler recording techniques. Furthermore, patients can be screened for the much more traumatic radiographic-medium visualization procedures. A considerable advantage of the images of this invention is that they look like present day arteriograms and venograms. Since the pictures have the same anatomical configuration that is revealed by X-ray arteriography, there is little new technique that need be learned to interpret them. They are somewhat easier to interpret, since bone shadows do not appear. The technique of this invention has the advantage of using available and more economical apparatus and employing the very sensitive and narrow-band continuous-wave doppler detector. For further refinement, using conventional electronic focusing phased array techniques an example of which is described in U.S. Pat. No. 3,090,030 using transmitting and receiving paths along coincident paths, the receiving and transmitting path can be automatically changed to accommodate changes in the depth of the vessel beneath the tissue.

Figure 6:
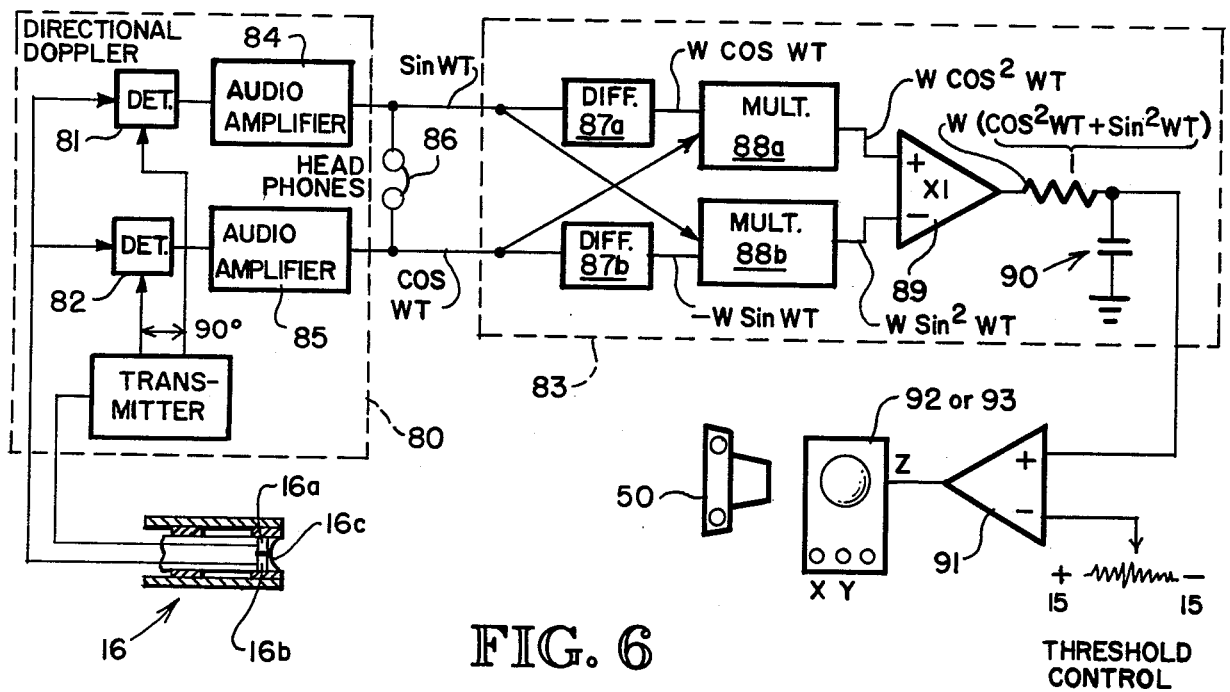
FIG. 6 is a circuit schematic utilized to eliminate undesirable venous flow signals and to provide oscilloscope intensity modulation proportional to velocity of the blood flow.
Figure 7B:
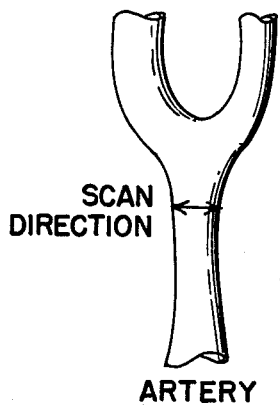
FIG. 7B is a sketch of the actual artery corresponding to the flow picture of FIG. 7A.

The improved electronic circuitry shown in FIG. 6 may be used as a direct replacement for the elements shown in FIG. 5. The conventional doppler transducer 16 has separate transmitting and receiving elements 16a and 16b which are shown connected to a conventional directional doppler circuitry 80. Ref. McLeod, F. D. Jr., A Directional Doppler Flowmeter, *Digest of the Seventh International Conference on Medical and Biological Engineering*, Stockholm, 1967. As in FIGS. 1–5 a concave spherical lens 16c focuses the sound a nominal 3 cms. from the transducer and provides a 1 mm. wide field (equivalent to less than 0.5, the diameter of the vessel being scanned, in the case illustrated the carotid artery, FIG. 7b). In this regard in the use of the invention for scanning other vessels than the carotid artery, the focusing again will be less than 0.5 the diameter of the vessel. The elements within the directional doppler have been shown to aid understanding how this type of conventional, commercially available equipment functions. The transmitter excites one half of the doppler transducer 16 while sending reference voltages to the two detectors 81 and 82 within the receiver. These reference voltages are 90° out of phase. Returning doppler signals from 16b are fed to both detectors and the resulting difference frequency output is an audio signal commonly referred to as the doppler signal which is 90° apart in the two channels. The waves coming out of the amplifiers 84 and 85 have the phase relationships of the sine and the cosine of the angle given by the product of the doppler freuency and time $\omega t$. Omega ($\omega$) (also shown in the drawings as W) has either a plus or minus sign depending on whether the blood flow is approaching or going away from the transducer. Head phones 86 are provided to listen to the signals while scanning. The circuit 83 shown connected to the directional doppler is an improvement of that described in Arts, M.G.J., and Roevros, J.M.J.G., On the Instantaneous Measurement of Blood Flow by Ultrasonic Means, *Medical and Biological Engineering*, 10, 23–24, 1972. The circuit consists of two differentiators 87a and 87b, which operate on the signals from amplifiers 84 and 85, respectively. Two multipliers 88a and 88b multiply respectively the signals from amplifier 85 and differentiator 87a and the signals from amplifier 84 and differentiator 87b. The products are given by the function $\omega\cos^2 \omega t$ and $-\omega\sin^2 \omega t$. The output of the multipliers each consists of a DC component and a frequency component. A conventional differential input operational amplifier adds the multiplier outputs and a conventional low pass filter 90 removes signals above about 200 Hz caused from noise, operator movement of the transducer, or any other signals not having the desired 90° phase difference relationship. The output of the low pass filter is a DC signal $\omega$. If the doppler frequency is positive, there will be a positive output voltage and if it is negative, the polarity will reverse. This voltage is passed to a threshold control 91 the output of which is used to intensity modulate the oscilloscope 92. The threshold control is an amplifier that saturates when a certain magnitude flow signal is received to produce a readable signal of maximum length to the oscilloscope during each spurt of blood flow. The circuit 83 will automatically select the flow from arteries if the polarities are arranged so that the polarity of the voltage from artery signals is correct to cause increasing intensity modulation of the oscilloscope in the normal case of venous flow being in the opposite direction from the artery flow.

Figure 9:
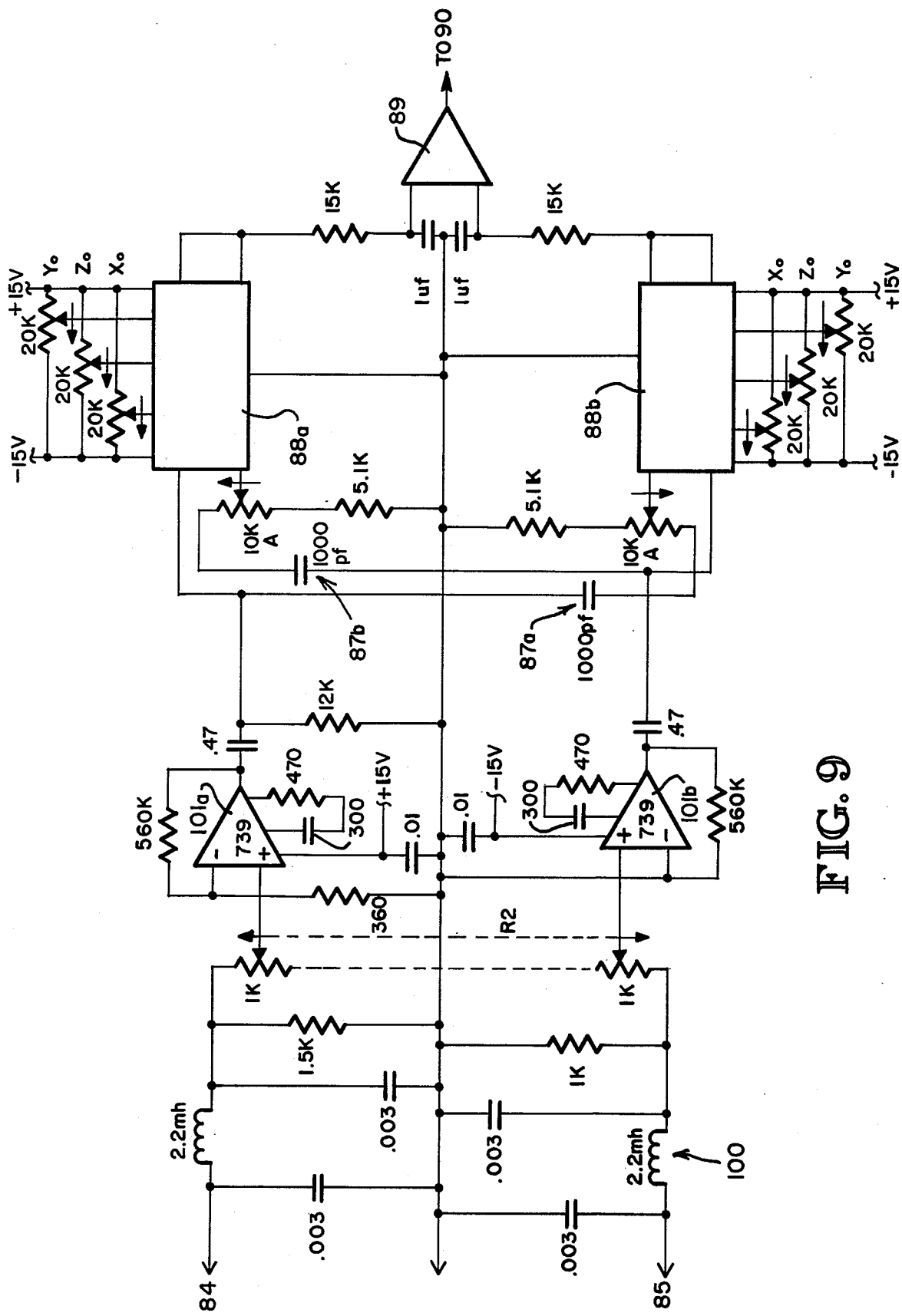
FIG. 9 is a more detailed schematic of circuit 83 of FIG. 6.

The preferred circuit 83 is illustrated in more detail in FIG. 9. Inputs from amplifiers 84 and 85 pass through filter 100 which removes external television signals and then pass to amplifiers 101a and 101b, respectively. The outputs from amplifiers 101a and 101b pass, respectively, to the differentiator circuits 87a and 87b and thence to multipliers 88a and 88b, respectively. Multipliers 88a and 88b are standard AD530J multipliers manufactured by Analog Devices, Inc., Rockford, Mass. Signals from amplifiers 101a and 101b are also passed to multipliers 88a and 88b, respectively.

The conventional storage oscilloscope 92 shown in FIG. 6 will intensify in response to a direct current signal so that the chopper modulator numbers 46 and 48 shown in FIG. 5, is not necessary.

Alternately, a display or color oscilloscope 93 which has a grey or color scale output can also be used without a threshold control 91. Such oscilloscopes are commercially available and produce a brightening or coloring of the screen which is in proportion to the value of the signal voltage on the Z axis terminal. The threshold control is not used with the grey or color scale oscilloscope since the magnitude of the flow velocity is desired to be observed throughout the spurt. The display on a grey or color scale oscilloscope would not display veins, for example, if the polarity of the output voltage from the multiplier were such that the oscilloscope would not intensify the direction of venous flow. The image displayed is blood flow in the arteries with a brightness or color proportional to the velocity of the blood flow.

The grey or color scale oscilloscope provides a significant advantage, particularly when dealing with stenosis (restrictions in the vessel) in which the near and far walls, i.e., perpendicular to scanning plane, of the artery approach each other to obstruct flow. The narrowing is not otherwise detected in the circuits of FIGS. 5 and 6. The head phones 86, however, detect an increase in velocity of blood flow as it passes the stenosis and a characteristic turbulence sound from immediately downstream of the stenosis and can be correlated to the location on the scan picture. The use of a grey scale or color oscilloscope 93, however, allows the continuous brightening or coloring of the display because the high velocity through the stenosis produces a higher frequency doppler signal which then produces a brighter area on the oscilloscope.

The detection of athersclerosis, where the walls of the vessel are thickened as by an accumulation of fats or plaque on or in the walls, is extremely valuable. This condition is detected by an increased amplitude of the low frequency audio signal in the headphones. When the wall is thickened and becomes less elastic, these low frequency signals are noticeably increased in amplitude.

Figure 8:
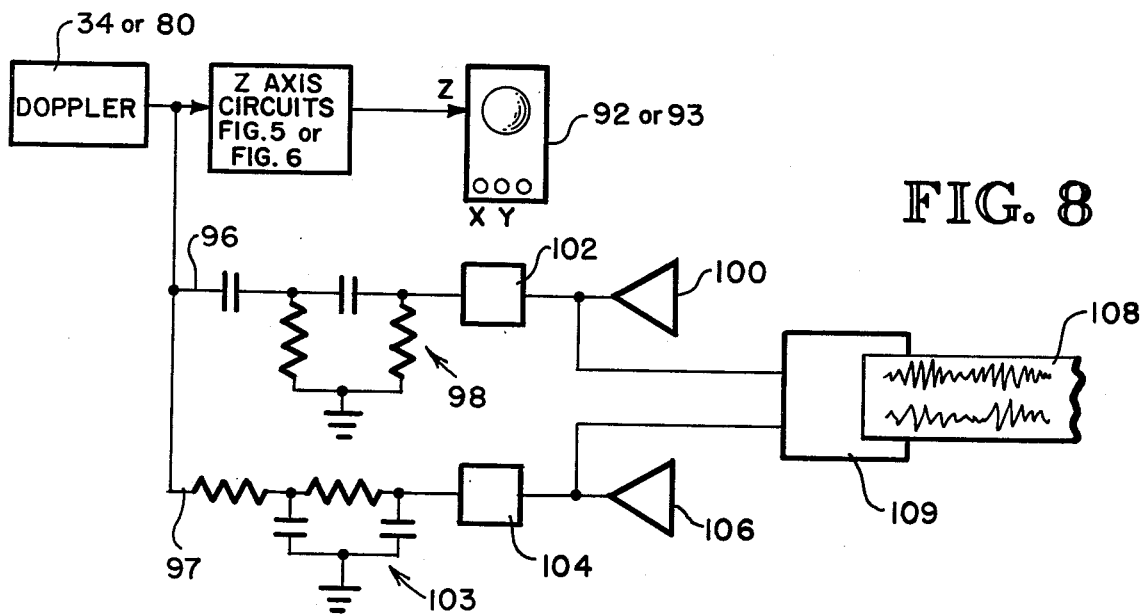
FIG. 8 is a preferred circuit for detecting certain atherosclerotic conditions in an artery.

It is an improvement in this application that the increased amplitude of these wall signals can be correlated automatically with the flow picture, to locate the area of plaque development. For this purpose, FIG. 8 shows a two channel audio listening and recording system. The audio output signal from either doppler 34 or 80 is split into two channnels 96 and 97. Channel 96 has a conventional high pass filter which passes frequencies above approximately 500 Hz which are listened to on the speaker 100 output in the conventional way for detecting audibly amplitude changes or velocity changes. The low frequency signals, however, are not reproduced well by normal audio circuitry so the second channel 97 is employed. The high pass filter 98 removes the generally louder audio doppler signals due to flow from the input of the amplifier 102. The low frequency sounds are passed by low pass filter 103 in channel 97 if their frequencies lie below, about 500 Hz. These are amplified in a low frequency amplifier 104 and presented on a conventional low frequency speaker 106 or recorded directly on chart paper 108 in a conventional recorder 109. This system will thus preserve for study the low frequency doppler signals which are of diagnostic significance for detecting the atherosclerosis. The useful range of filter cutoff frequencies is 100–1000 Hz.

FIGS. 10–14 show still another improvement of the arteriographic scanning system. In this embodiment multiple beams are employed simultaneously to produce a picture which covers one diameter of the artery all at one time, rather than requiring that the operator scan, i.e. move, a single beam across the diameter. Th simultaneous viewing of a number of points across the vessel is accomplished by employing a multiplicity of focused sound beams each of which must meet the resolution requirements less than about 0.2 mm. for the carotid artery or otherwise less than 0.5 diameter of the vessel under investigation. Another alternative is to rapidly scan a single beam across the vessel by use of time multiplexing to obtain the same result as the use of multiple beams to be described.

The purpose of the device of FIGS. 10–14AA is to allow a complete vessel diameter to be recorded during each position of the transducer carrier so that the operator need only move such diameter displaying transducer carrier longitudinally along the length of an artery. A complete picture will be produced in far less time than is presently required using a single transducer. This will be significant advantage in reducing the disturbing effects of motion of the patient, and allowing the operator to take multiple views from different angles if the patient is found to have twisted blood vessels.

A typical multiple beam system employs multiple transducers 16AA housed in close spaced proximity to each other in a carrier (array transducer) 110 so that many sound beams lie next to each other in space. Since a single transducer is much wider than the beam, there are a number of practical problems in doing this. FIGS. 14 and 14A show a way in which these multiple transducers can be interlaced. The array transducer 110, of an N member of unfocused elements is interconnected through conventional delay lines or phase shifters 112 to form a number of separate beams in space. Each of the beams employs all or only a few of the unfocused transmitting-receiving elements 16A of the transducer, and we will use M to indicate the number of beams actually formed. In FIG. 14 only one set of elements and one set of delay lines for simplicity are shown schematically, although in the case of a doppler system a separate set of delay lines for the transmitting half of the transducer, and another set for receiving half may be employed. This technique of forming multiple beams is well known and for an analogous use with an array antena, see Skolnik, M. I., *Introduction to Radar System,* pp. 301–305, McGraw Hill Book Company, 1962. It is possible to achieve as many beams as there are elements in the transducer, that is have M equal N, see Butler, J. and Lower, R., "Beam Forming Matrix Simplifies Design of Electronically Scanned Antenna" *Electronic Design,* pp 170–173, Apr. 12, 1961.

Also shown in FIG. 14A is a schematic illustration of the N array transducer configuration used in one preferred manner with delay lines 112A, which are part of block 112 of FIG. 14, or phase shifter for focusing. Each transmitting-receiving element 16A is coupled with two other elements with the center element coupled through the delay line or phase shifter circuit 112A. As is well known in the art the purpose for the delay is to allow the opposite adjacent beams to travel the longer distances and arrive at the desired focusing point at the same time or in phase with the beam from the center element.

As is readily understood, of course, delay lines or phase shifters are not needed in the condition of closely spaced transducers that have lens focusing as for example described with reference to FIGS. 1 and 6.

In FIG. 14 the transducer is shown pointed at an artery with the M beams intersecting across a diameter. The beams are formed by taking the output voltage of the transmitter of the doppler 34 and connecting it through M buffer amplifiers 114 to the beam forming terminals of the delay line or phase shifter elements. The buffer amplifiers prevent the connections to the transmitter from connecting together all of the beam terminals. The received signals are picked up by the same or a different set of transducer elements, fed through identical delay line structures to form the appropriate number of beams, and each beam output terminal is fed to its associated receiver 116. Each of these receivers now functions in exactly the same manner as individual receivers, discussed previously, producing an output voltage whose value is proportional to the doppler shift, and which has preserved the sign of the flow direction.

A different set of circuits is required to present the output of each of these M receivers 116 on the single beam oscilloscope display 92 or 93 at the proper position in the XY coordinate system used for positioning a spot. FIG. 14 shows a multiplexer consisting of a simple M position single-pole switch 118 in which a stepping relay connects each of the receivers, in turn, to the display device. The dashed line shows a connection necessary between the multiplexer and the spot positioning circuits which must move the spot to the appropriate position on the screen so that the spot position corresponds to the position in space of the ultrasonic beam from which the doppler signal is being recorded. Two systems for doing this are shown in FIGS. 10–13.

FIG. 10 shows the simplest case in the use of a multiple beam transducer. Here the transducer is affixed to the end of the rho theta scanning arm 60 shown in FIG. 1. The transducer 110 is mounted on the end of the scanning arm, 60, in the same manner as the original transducer, 59. Each beam sent out by this transducer corresponds to a different value for the length of the radius arm, rho. A simple way of instrumenting this change in rho is shown in the circuit diagram of FIG. 11 which is identical in function to the circuit in FIG. 2. A stepping multiplexer is shown which effectively changes the value of the battery voltage by a small increment corresponding to the rho-coordinate position of each of the M beams of the array. It is shown connected to the terminal which would correspond to the beam which is the furthest from the pivoting axis of the arm 60. As the arm steps across the contacts, a voltage corresponding to the particular value of rho (distance along arm 60) which corresponds to each beam position is fed to the XY circuitry to produce a corresponding change in X and Y positions of the spot on the oscilloscope.

Another possible realization of the circuit which does not involve mechanical scanning such as in unit 120 is to use an electronic "Staircase" generator which generates the staircase voltage shown in the wave form in FIG. 11, which would be added to the battery voltage. Trigger signals indicating each step of this staircase are independently generated and used to control both the value of the staircase voltage and the position of the Z axis multiplexer shown in FIG. 14. This all electronic system is more convenient and is the basis for the explanation of the more general spot-position control circuitry shown in FIG. 13.

Preferably the operator is able to select the direction of the scanned diameter by rotating the transducer 110 located at the end of the arm, 60, as shown in FIG. 12. Here, the scanning transducer 110 with its N elements is mounted on a cross-axis on the end of the arm. Also mounted on the axis is a resolver 122, i.e.; a sine-cosine magnetic resolver or a sine-cosine potentiometer. The circuitry shown here is designed to change the position of the spot which represents the end of the arm, 60, according to which beam is being connected to the Z-axis of the oscilloscope. The conventional resolver 122 converts the input voltages from generator 123 into two component voltages which are the X and Y coordinates of the rotated transducer position. The change required in the X and Y coordinates are shown in equations in FIG. 13. The voltage E is a staircase voltage whose overall magnitude is proportional to the angular displacement of the corresponding transmitting-receiving elements of the multiple beam transducer 110 on the end of the arm. A staircase is shown with M values, starting with a fixed negative polarity corresponding to the maximum shortening of the arm, 60, and ending with an equal positive polarity corresponding to the maximum lengthening of the arm, 60. The voltage of the ends of the staircase are only equal in the case of an odd number of beams, and for the purpose of this description the diagrams are drawn for an M equal to 7. The staircase is generated by the E generator 123 shown in the block diagram in FIG. 13. This is triggered by the trigger output from the Z-axis multiplexer 118 so that when the wave form has the value corresponding to a particular beam, the Z-axis multiplexer is feeding the appropriate voltage from that beam into the Z axis of the oscilloscope. The staircase voltages are fed to the resolver 122 which produces ΔX and ΔY voltages proportional to the sine and cosine of the angle between the rotatable transducer 110 and the horizontal line 124 shown in FIG. 12. These ΔX and ΔY wave forms represent corrections to the X and Y position. Each is a staircase voltage whose amplitude is modulated by the sine and cosine of the angle φ. These voltages are added to the X and Y coordinate voltages obtained from the circuit of FIG. 2, for example. The new X and Y voltages, X' and Y', are fed to the display oscilloscope. See FIG. 13.

The embodiments of the invention in which a particular property or privilege is claimed are defined as follows:

1. A method of detecting the flow picture in vessels in human tissue containing moving sound scatterers, comprising:
   transmitting and receiving the reflections of an ultrasonic continuous sound wave focused to a width of less than half the diameter of the vessel at a depth where sound scatterers are located through a sound transmitting medium into the tissue in a small region expected to contain the vessels being investigated, thus receiving flow information from said small region to the exclusion of surrounding regions;
   detecting the presence of the moving scatterers in the vessels within said small region using the doppler effect;
   systematically transmitting and receiving over the desired vessel to produce a clearly defined pattern; and
   converting the ultrasonic reflected signals to a visually detectable output.

2. The method of claim 1, said step of transmitting and receiving including transmitting and receiving along paths intersecting at said localized region.

3. The method of claim 2 wherein said step of systematically transmitting and receiving includes sweeping across the artery being investigated at extremely fine intervals to produce a generally solid line configuration of the vessel.

4. The method of claim 1, said step of transmitting and receiving including transmitting and receiving along coincident paths.

5. The method of claim 1, said step of converting including permanently photographing the visually detectable output.

6. The method of claim 1 wherein said vessels are arteries and the sound wave is focused in the order of 1 mm or smaller.

7. The method of claim 1, including the step of correlating the velocity of the scatterers with the location in the vessel at which the flow information is determined for identifying stenosis of the vessel.

8. The method of claim 1, said step of converting the ultrasonic reflected signals including recording all recordable flow signals.

9. The method of claim 1, said step of converting the ultrasonic reflected signals including recording all recordable flow signals above a predetermined threshold level.

10. A method of detecting the flow picture in vessels in human tissue containing moving sound scatterers, comprising:
    transmitting and receiving the reflections of an ultrasonic continuous sound wave focused to a width of less than half the diameter of the vessel through a sound transmitting medium into the tissue in a small region expected to contain the vessels being investigated, thus receiving flow information from said small region to the exclusion of surrounding regions;

detecting the presence of the moving scatterers in the vessels within said small region using the doppler effect;

systematically, repeatedly transmitting and receiving over portions of the desired vessel until sufficient portions have been covered to produce a clearly defined pattern of the flow of the moving scatterers within the vessel; and converting the ultrasonic reflected signals to a visually detectable output, said step of detecting the presence of the moving scatterers including isolating first and second signals reflected from scatterers moving in a desired direction, said step of converting the ultrasonic reflected signals including differentiating the first and second signals andd then multiplying the first signal by the differentiated second signal and multiplying the second signal by the differentiated first signal, differentially adding the products of the multipliers, and removing low frequency noise.

11. A method of detecting the flow picture in vessels in human tissue containing moving sound scatterers, comprising:

transmitting and receiving the reflections of an ultrasonic continuous sound wave focused to a width of less than half the diameter of the vessel through a sound transmitting medium into the tissue in a small region expected to contain the vessels being investigated, thus receiving flow information from said small region to the exclusion of surrounding regions;

detecting the presence of the moving scatterers in the vessels within said small region using the doppler effect;

systematically, repeatedly transmitting and receiving over portions of the desired vessel until sufficient portions have been covered to produce a clearly defined pattern of the flow of the moving scatterers within the vessel; and converting the ultrasonic reflected signals to a visually detectable output, including the step of separately recording low-frequency, high-amplitude audio signals correlated with the location in the vessel at which the flow information is determined to locate atherosclerotic vessel conditions.

12. The method of producing a flow picture of the moving scatterers in a human vessel, comprising transmitting and receiving the reflections of several ultrasonic sound waves spaced across the diameter of the vessel and each focused in the order of one-half a diameter of the vessel or less, detecting the presence of the moving scatterers using the doppler effect, converting the ultrasonic reflected signals to a visually detectable output to produce a full diameter flow picture, and moving the receiving and transmitting beams longitudinally along the vessel to obtain a flow picture of the entire vessel.

13. The method of claim 12, including the step of rotating the spaced sound waves relative to the longitudinal axis of the vessel for obtaining a flow picture as the vessel changes direction within the tissue.

14. A method of detecting the location and shape of the interior walls of vessels in human tissue containing moving sound scatterers, comprising:

transmitting and receiving the reflections of an ultrasonic continuous sound wave focused in the order of 1 mm or smaller to a localized region at a particular depth to maximize their sensitivity through a sound transmitting medium into the tissue in a region expected to contain the vessels being investigated;

detecting the presence of the moving scatterers in the vessels using the doppler effect;

systematically transmitting and receiving over the desired vessel to produce a clearly defined pattern; and converting the ultrasonic reflected signals to a visually detectable output.

15. Apparatus for detecting the flow picture in vessels containing moving sound scatterers, comprising:

means for transmitting and receiving ultrasonic continuous sound waves focused to a localized region at a particular depth into the tissue in which the vessel is located, thus receiving flow information from said small region to the exclusion of surrounding regions;

said transmitting and receiving means including focusing means for focusing the waves to a width of about one-half the diameter of the vessel or less;

means for producing an output signal representative of sound waves reflected only from moving scatterers;

means for scanning the transmitting and receiving means over the medium to define a pattern of the vessel; and means for converting the output signal to a visually intelligible form.

16. The apparatus of claim 15, said focusing means being operable to focus the waves to 1 mm or less.

17. The apparatus of claim 15, said scanning means including an arm pivotally mounted at one end, a doppler blood flow detecting transducer connected to the free end, and having accurate position sensors attached thereto to produce exact X and Y coordinates corresponding to the X and Y coordinates on an oscilloscope.

18. The apparatus of claim 15, said scanning means including an arm movable along its horizontal axis for establishing a rho coordinate, movable in a horizontal arc for the theta coordinate and circuits to establish the X and Y coordinates from said rho and theta coordinates, said arm being movable in a vertical arc for moving over the irregularities of the patient's tissue.

19. The apparatus of claim 15, said means for connecting the output signal to a visually intelligible form including means for displaying the output signal on a gray or color scale oscilloscope to produce an image whose picture characteristic is proportional to the velocity of the moving scatterers for detecting stenosis.

20. The apparatus of claim 15, said means for transmitting and receiving including multiple transducers closely spaced in a line across a diameter of the vessel, said means for scanning including means for automatically, simultaneously energizing said spaced transducers for providing spaced beams across the entire diameter of the vessel, said means for converting including correlating said spaced beam receiving reflection signals with the location of the respective transducer to automatically produce a picture of a full diameter whereby movement only longitudinally of the vessel produces a full flow picture of the vessel.

21. The apparatus of claim 20, said scanning means further including means for pivoting said spaced transducers relative to the longitudinal axis of the vessel, and said converting means including means for correlating the received reflected signals with the angular displacement of the transducers to accommodate twist in the vessels.

22. Apparatus for detecting the location and shape of vessel walls containing moving sound scatterers, comprising:
- means for transmitting and receiving ultrasonic continuous sound waves focused to a localized region at a particular depth to maximize their sensitivity into the tissue in which the vessel is located;
- said transmitting and receiving means including focusing means for focusing the waves to a width of about 1 mm or less;
- means for producing an output signal representative of sound waves reflected only from moving scatterers;
- means for scanning the transmitting and receiving means over the medium to define a pattern of the vessel; and
- means for converting the output signal to a visually intelligible form.

23. Apparatus for detecting the flow picture in vessels containing moving sound scatterers, comprising:
- means for transmitting and receiving ultrasonic continuous sound waves focused to a localized region at a particular depth into the tissue in which a vessel is located, thus receiving flow information from said small region to the exclusion of surrounding regions;
- said transmitting and receiving means including focusing means for focusing the waves to a width of about one-half the diameter of the vessel or less,
- means for producing an output signal representative of sound waves reflected only from moving scatterers;
- means for scanning the transmitting and receiving means over the tissue in which the vessel is located to define a pattern of the flow picture within the vessel to determine the shape of the inside of a longitudinal section of the vessel; and
- means for converting the output signal to a visually intelligible form, said means for producing an output signal including means for isolating only reflections from scatterers moving in one direction, said isolating means including first and second detectors for receiving the reflected signals and for combining the signals with generated signals of 90° phase shift, first and second differentiating means for differentiating said first and second combined signals, respectively, first and second multipliers for multiplying said combined signal with said first differentiated signal and multiplying said first combined signal with said second differentiated signal, respectively, means for differentially adding the products of the two multipliers, and low-pass filter means for removing undesirable low-frequency signals.

24. Apparatus for detecting the flow picture in vessels containing moving sound scatterers, comprising:
- means for transmitting and receiving ultrasonic continuous sound waves focused to a localized region at a particular depth into the tissue in which a vessel is located, thus receiving flow information from said small region to the exclusion of surrounding regions;
- said transmitting and receiving means including focusing means for focusing the waves to a width of about one-half the diameter of the vessel or less,
- means for producing an output signal representative of sound waves reflected only from moving scatterers;
- means for scanning the transmitting and receiving means over the tissue in which the vessel is located to define a pattern of the flow picture within the vessel to determine the shape of the inside of a longitudinal section of the vessel; and
- means for converting the output signal to a visually intelligible form, said means for converting the output signal including separate channel means for isolating low-frequency, high-amplitude audio signals representative of vessel wall movement, and means for displaying the audio signal correlated to the location of which the flow information is determined for identifying atherosclerotic regions of the vessel.

* * * * *